United States Patent [19]

Mueller

[11] 4,289,131
[45] Sep. 15, 1981

[54] SURGICAL POWER TOOL

[75] Inventor: Rene E. Mueller, Osceola, Ind.

[73] Assignee: Ergo Instruments, Inc., Granger, Ind.

[21] Appl. No.: 39,756

[22] Filed: May 17, 1979

[51] Int. Cl.³ .............................................. A61B 17/00
[52] U.S. Cl. .............................. 128/303 R; 128/305.1; 277/DIG. 6
[58] Field of Search ..................... 128/310, 305.1, 305, 128/303 R, 755; 277/229, DIG. 6, 91, 92; 279/9 R, 97, 76

[56] References Cited

U.S. PATENT DOCUMENTS

| 2,655,921 | 10/1953 | Haboush | 128/305.1 |
| 3,921,985 | 11/1975 | Fimml | 277/22 |
| 4,014,342 | 3/1977 | Staub et al. | 128/305.1 |

Primary Examiner—Robert W. Michell
Assistant Examiner—Michael H. Thaler
Attorney, Agent, or Firm—Marmaduke A. Hobbs

[57] ABSTRACT

A surgical power tool in which a quick-lock latch mechanism permits attachment and removal of the drive shaft assembly with one hand and a seal arrangement effectively seals moisture from the bearing and motor compartments, yet creates only minimal drag on the motor. The power unit portion has a female end which receives the male end of the drive shaft assembly. Outwardly extending pins from the male portion pass through aligned notches in a rotatable cap portion and in the female end, and are locked in place by rotation of the cap. The seal consists of a nylon bushing on the shaft, slightly less in diameter than the internal bore of the tool, and a mica seal fitted within the bore but loosely on the shaft, the bushing and mica seal seating on each other when the tool is shut off to maintain an effective seal while the tool is inoperative.

10 Claims, 5 Drawing Figures

SURGICAL POWER TOOL

During the course of a surgical operation, electrical or other power surgical tools are often used by the surgeon to perform various procedures. Several different types of instruments may be required during an operation, and hence a number of changes may be required whereby different instruments are attached to a single power unit. Often the need for a different instrument arises immediately after the use of another power instrument. In these situations rapid change of the surgical instrument on the motor or power unit is essential to the welfare of the patient. Previous designs for power surgical tools have not provided ease in changing of the instruments. The attachment mechanism must rigidly lock the instrument in place so that no false movement of the assembled tool occurs while in use by the surgeon. To meet the requirement of a substantially rigid assembly, previous designs for locking mechanisms have been complex, frequently requiring two hands to lock and unlock the mechanism, and therefore the surgeon must either have both hands free and available to do so or must hand the assembled tool to a surgical assistant who can then change the instrument and, in return, hand it back to the surgeon. This can be very time consuming, and hence very detrimental to the welfare of the patient. It is desirable to have a surgical power tool with a latching mechanism which can be operated by one hand to release the instrument quickly and which can, just as easily, quickly lock a new instrument in place.

A second principal problem which arises in the use of power surgical tools is caused by the frequent contact with moisture such as blood, water, steam or the like, which is very prevalent in the surgical suite or operating room. These or other contaminants may come in contact with the tool and often seep into the bearings or power compartments, thereby fouling the bearings or causing the power unit to short. One of the principal difficulties in designing a seal for a surgical tool to prevent the seepage of moisture is that although the seal must be tight enough to keep out moisture such as steam or water, it cannot be so tight as to cause substantial drag on what necessarily is a relatively small motor or power unit, since frequently the entire unit, including the bearing and motor compartment, is hand held.

It is therefore one of the principal objects of the present invention to provide a surgical power tool which can be quickly attached to the particular surgical instruments needed, and which will provide an effective seal keeping out moisture and other contaminants from the bearing and motor compartment.

Another object of the present invention is to provide a surgical power tool having a latching mechanism which can be operated with one hand in both attaching and detaching the drive shaft assembly and instrument portion of the tool from the power unit portion, thereby freeing one of the surgeon's hands to control the patient or hold other instruments or devices which he may at the time be using, and which attaches or detaches in a single, simple movement requiring minimal time to perform.

Still another object of the present invention is to provide a surgical power tool having a locking mechanism which locks in place automatically when the power unit is attached to the drive shaft assembly and instrument portion, and which locks securely, providing a substantially rigid assembled tool having little or no play, thereby creating no false movement of nor permitting play in the instrument head when in contact with the patient.

A further object of the present invention is to provide a surgical power tool having a sealing mechanism which will keep out moisture and other contaminants, thereby sealing the bearing and motor compartments from possible fouling or shorting, yet which will not cause significant drag on the rotation of the power shaft or motor during the operation of the tool.

A still further object of the present invention is to provide a surgical power tool having a quick lock mechanism and an effective seal keeping contaminants from the bearing and motor compartments, yet which is small and light in weight, is capable of being hand held, and is easily operated and maneuvered by one hand of the surgeon, and which is capable of being sterilized in conventional sterilizing devices and mechanisms.

Further objects and advantages of the present invention will be obvious from the following detailed description and drawings wherein.

Figure 1:
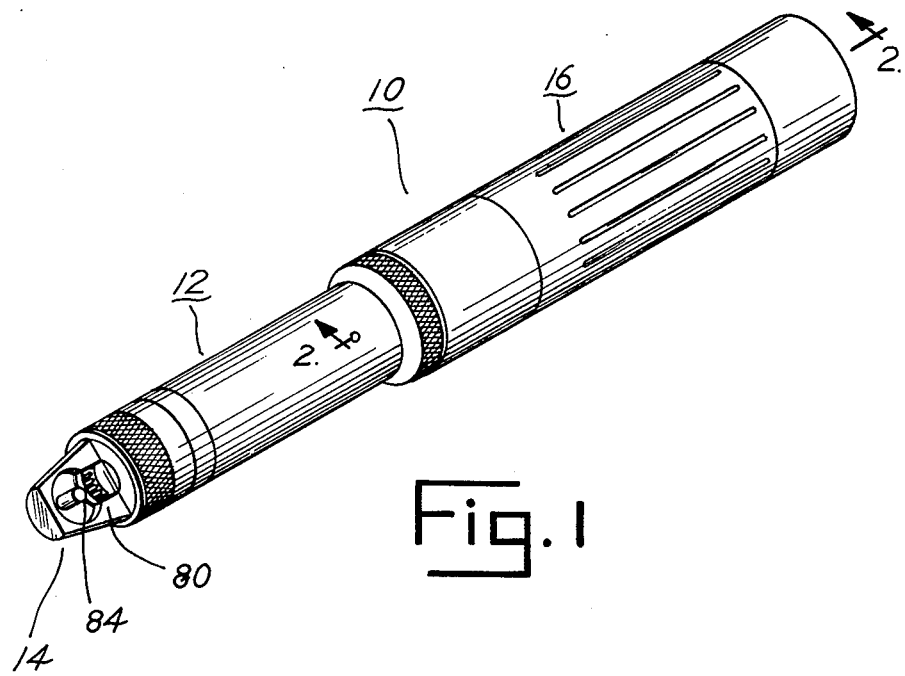
FIG. 1 is a perspective view of an assembled surgical tool having the quick-lock latch mechanism and minimal drag type seal of the present invention.
Figure 2:
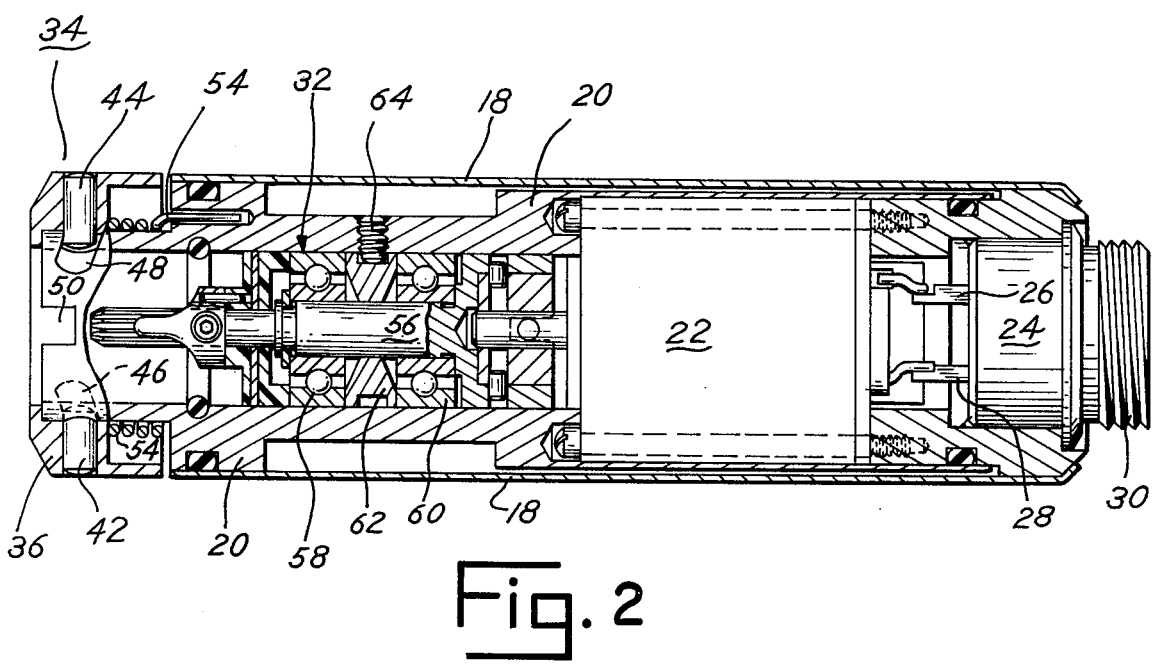
FIG. 2 is an enlarged longitudinal cross sectional view of the power unit portion of the surgical tool shown in FIG. 1, the cross section taken on line 2—2 of FIG. 1.
Figure 3:
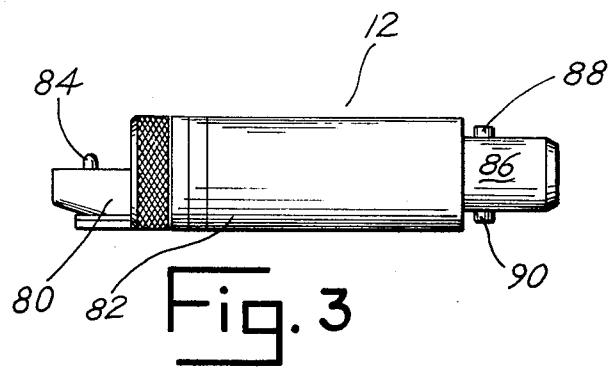
FIG. 3 is a side elevational view of the drive shaft assembly of the surgical tool shown in FIG. 1.

Referring more specifically to the drawings, and to FIG. 1 in particular, numeral 10 indicates a surgical power tool employing the quick lock mechanism and minimal drag seal design of the present invention, and consists of a hand piece and drive shaft assembly 12 to which the surgical instrument, such as a blade, drill or the like, is attached at the end indicated generally by numeral 14, and a drive unit assembly 16 to which the other end of the drive shaft assembly is operatively connected. Drive unit 16 consists of an outer housing 18 extending over substantially the entire length of the drive unit and enclosing all of the inner parts thereof. An inner sleeve 20 of varying thickness and shape is disposed within the inner wall of housing 18. Within inner sleeve 20 is a motor assembly 22 having at its rearward portion a connector assembly 24 through which the surgical tool is connected to the power supply in the operating room. The connector assembly consists essentially of electrical contacts 26 and 28 and a threaded attachment portion 30 with which the instrument is threadedly attached to an electrical supply cord.

Immediately forward of an operatively connected to the motor assembly 22 is an intermediate shaft assembly 32 which contains the seal 33. The forwardmost portion of drive unit 16 of medical instrument 10 consists of a locking mechanism 34 comprising a rotatable generally annular shaped cap 36 having in its top portion two slots 38 and 40. Two pins 42 and 44 extend from cap 36 inwardly, passing through inclined slots or grooves 46 and 48 of inner sleeve 20. Extending slightly rearward from the forwardmost end of inner sleeve 20 are two slots 50 and 52. When cap 36 is rotated to the open position, slots 38 and 40 of cap 36 align with slots 50 and 52 of inner sleeve 20. Grooves 46 and 48 are slightly inclined so that, as cap 36 is rotated to its open position, pins 42 and 44, traveling in grooves 46 and 48, move slightly toward the front of the tool. This moves cap 36 slightly away from housing 18 as cap 36 is rotated to its open position. A spring 54 attached to cap 36 and inner sleeve 20 automatically returns cap 36 to its closed position by rotating the cap and causing pins 42 and 44 in grooves 46 and 48 to draw the cap back toward housing 18, when cap 36 is released.

Intermediate shaft assembly 32 consists of a shaft 56 extending forwardly from and operatively connected to motor unit 22 and journaled in bearings 58 and 60 which are separated by a spacer 62 held in position by a set screw 64. A driver 66 is attached to shaft 56 and is held by a set screw 68. The seal 33 separating the bearings and motor compartment of drive unit 16 from the exposed area forwardly thereof consists of a nylon seal bushing 70 which is closely fitted to and rotates with shaft 56, being held to driver 66 by a spring pin 71. The external diameter of seal bushing 70 is slightly less than the internal bore of sleeve 20, and the bushing will therefore rotate freely within the sleeve. A mica seal 72 is disposed just rearward of seal bushing 70 on shaft 56. Mica seal 72 fits snugly within the internal bore of sleeve 20; however, the diameter of the hole in mica seal 72 through which shaft 56 passes is slightly larger than the diameter of shaft 56 so that, as the shaft turns, mica seal 72 will not turn. A seal retainer 74 behind mica seal 72 maintains the position of seal bushing 70 and mica seal 72. Thus, an effective seal is created between the shaft 56 and seal bushing 70 and an effective seal is created between the bore of sleeve 20 and mica seal 72. Minimal drag is created in that the bushing 70, which is seated firmly on shaft 56, does not drag on the bore of sleeve 20 in that the overall diameter is slightly less than that of the bore, and mica seal 72, which fits snugly within the internal bore of sleeve 20, has no drag on shaft 56, since the hole thereof through which shaft 56 extends is slightly larger than the diameter of the shaft. When seal bushing 70 and mica seal 72 are firmly seated on one another, an effective seal is created between driver 66 and the bearing and motor compartment. Although seal bushing 70 fits tightly on shaft 56, it may also move somewhat axially so that during operation of the tool, seal bushing 70 moves slightly away from mica seal 72. In this way no drag is created between seal bushing 70 and mica seal 72 during the operation of the tool. However, when the tool is turned off, a static electric field which is created by the rotation of seal bushing 70 in front of mica seal 72 causes the two parts to be attracted to each other, thereby drawing seal bushing 70 rearwardly toward mica seal 72 and seating one upon the other. Thus an effective seal is created within the bore, around the shaft and between seal bushing 70 and mica seal 72 when the tool is turned off.

Figure 4:
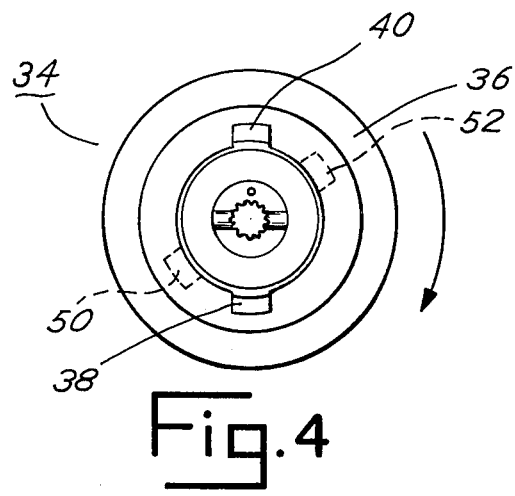
FIG. 4 is an end elevational view of the locking mechanism of the surgical tool shown in FIGS. 1 and 2, with some of the hidden features shown by broken lines.
Figure 5:
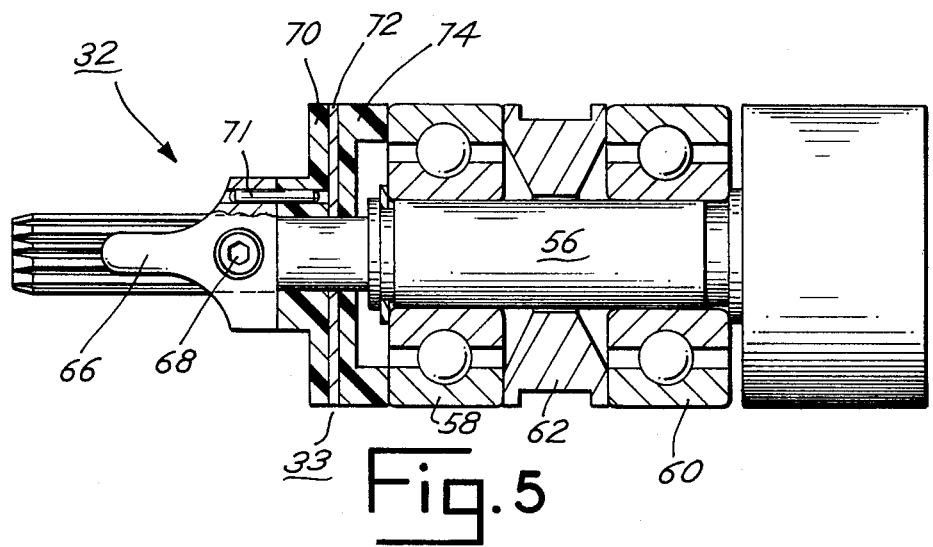
FIG. 5 is an enlarged cross sectional view of the intermediate shaft assembly of the surgical tool as shown in FIG. 2.

Hand piece and drive shaft assembly 12, which can be any one of a number of different surgical tools, consists of an instrument attachment head 80 and an external housing 82 which encloses a drive mechanism 84. The lower end of housing 82 is machined to a diameter to slip through the center opening in cap 36 and fit within the inner bore of sleeve 20, this portion of housing 82 being indicated generally by numeral 86. Two opposing pins 88 and 90 extend outwardly from the machined portion 86 of housing 82 and are of a size and are positioned in respect to each other to slide through slots 38 and 40 of cap 36 and to rest in slots 50 and 52 of inner sleeve 20 when the tool is assembled and the cap is rotated by spring 54 in the counterclockwise direction as viewed in FIG. 4.

In the use and operation of a power surgical tool employing the quick-lock latch mechanism, and the minimal drag moisture seal design of the present invention, a surgical blade, drill or other device is connected to the instrument attachment head 80 of drive shaft assembly 12. Machined portion 86 of drive shaft assembly 12 is then inserted in the forward portion of drive unit 16, and pins 88 and 90 are positioned in slots 38 and 40 of annular cap 36. Pins 88 and 90 will rest on the upper surface of sleeve 20, because spring 54 holds cap 36 in a position such that slots 38 and 40 are not in alignment with slots 50 and 52 of inner sleeve 20. A slight rotation of drive shaft assembly 12 will rotate cap 36 as pins 88 and 90 contact the sides of slots 38 and 40. When cap 36 is rotated so that slots 38 and 40 align with slots 50 and 52, pins 88 and 90 will drop inlet slots 50 and 52. As cap 46 is rotated, pins 42 and 44 travel in grooves 46 and 48 which are slightly inclined, thereby moving cap 36 slightly away from sleeve 20. Spring 54 will return cap 36 to its closed position when the cap is released, by drawing it back toward sleeve 20. As it is drawn back, cap 36 will rotate as pins 42 and 44 travel in reverse direction in inclined grooves 46 and 48. Pins 88 and 90 at this point are in slots 50 and 52, and since cap 36 has rotated to its closed position, slots 38 and 40 no longer align with slots 50 and 52; therefore, drive shaft assembly 12 is attached firmly to drive unit 16 by cap 36. Normally, slots 50 and 52 are of a size only slightly larger than pins 88 and 90 so that there is very little movement of pins 88 and 90 in slots 50 and 52 in the locked position, making the tool a rigid assembly of its parts.

When it is desired to remove drive shaft assembly 12 from drive unit 16, cap 36 can be rotated with one hand so that slots 38 and 40 align with slots 50 and 52. A knurled surface on the periphery of cap 36 makes an effective surface to be gripped between the thumb and index finger. Drive shaft assembly 12 and pins 88 and 90 thereof will then easily slide out of the aligned slots. Thus, the surgeon while holding the tool with one hand can rotate cap 36 and allow drive shaft assembly 12 to disengage drive unit 16 and fall into a receiving pan or into a surgical assistant's hand. The surgical assistant who is handing the new instrument, which is attached to another drive shaft assembly, to the surgeon may simply insert it directly into drive unit 16 and, when the surgeon releases the cap, it rotates counterclockwise as viewed in FIG. 4 to lock the drive shaft assembly in place. This is no more difficult nor more time consuming than the conventional hand-to-hand passing of surgical instruments between the surgical assistant and surgeon, which normally takes place during an operating procedure. Attachment and detachment are simple and quick, and the surgeon will at all times have one hand free to hold other instruments if required.

During sterilization of the medical tool, which normally takes place at approximately 275°, seal bushing 70 expands slightly to contact the inner bore of sleeve 20. Upon cooling of the tool, seal bushing 70 shrinks slightly, thereby allowing free movement of the seal within the bore but allowing very little in the way of moisture or other contaminants to leak between the inner bore of sleeve 20 and seal bushing 70. If any moisture or contaminant should get through, it is sealed off by mica seal 72, which is seated against the inner wall of sleeve 20. During the operation of the tool, seal bushing 70 slides axially away from mica seal 72, hence eliminating any drag between mica seal 72 and seal bushing 70. Since seal bushing 70 is seated snugly on shaft 56 and rotates with it, whereas mica seal 72 is seated firmly within the inner bore of sleeve 20 and does not rotate with the shaft, no drag occurs between any rotating and nonrotating parts. The rotation of bushing 70 in front of seal 72 creates a slight static electric field which, when the tool is shut off, attracts seal bushing 70 to mica seal 72. Thus, when the tool is turned off, a complete seal is created between the external portions and the bearing and housing compartment. Seal bushing 70 seals the shaft area, and mica seal 72 seals the bore of sleeve 20, and since seal bushing 70 and mica seal 72 seat firmly on each other, there is no space through which moisture can pass. Yet, when operating, as seal bushing 70 moves away from mica seal 72, neither is seated firmly on drive shaft 56 or sleeve 20; therefore, since seal bushing 70 and mica seal 72 are also not seated on each other, no drag is created on drive shaft 56.

Although the seal and quick lock mechanism have been shown to operate on an electrical surgical instrument, they can also be employed on other instruments such as pneumatically powered ones. The latching mechanism will work effectively wherever the quick lock, quick release type connection is desired in such instruments, and the seal design will work effectively under all normal operating conditions encountered in an operating room.

Although only one embodiment of my surgical power tool has been disclosed in detail herein, various changes can be made without departing from the scope of the present invention.

I claim:

1. A surgical power tool comprising a drive unit including an outer housing, an inner sleeve disposed therein, a power supply unit in said sleeve, a bearing in said sleeve, an intermediate shaft operatively connected to said power unit and journaled in said bearing in said sleeve, and a seal structure on said shaft and in said sleeve for excluding moisture from said power supply unit; and a drive shaft assembly releasably attached to said drive unit and having a portion of a diameter slidable into said sleeve, a slot in the forward end edge of said sleeve, and a pin projecting outwardly from said portion of said drive shaft assembly and slidable into said slot when said portion is inserted in said sleeve, a latching mechanism for securing said drive shaft assembly to said drive unit, said mechanism having an annular shaped rotatable cap around said sleeve and having at least one slot therein for registering with the slot in said sleeve, and a groove in said sleeve inclining outwardly in the direction in which said cap is rotated to align said slots, and a pin extending inwardly from said cap into said inclined groove for positioning said cap to firmly hold said drive shaft assembly in said sleeve, and an instrument attachment head on said drive shaft assembly for receiving a medical instrument to be operated by said drive unit.

2. A surgical power tool as defined in claim 1 in which a spring is disposed between said cap and said sleeve and is attached to said cap to return said cap to a position in which said slots are in misalignment.

3. A surgical power tool as defined in claim 2 in which said seal structure comprises first and second seals, said first seal being seated on and rotatable with said intermediate shaft and of an overall diameter slightly less than the internal bore of said sleeve, and said second seal being seated against the internal surface of said sleeve and having a hole through which said intermediate shaft passes slightly larger than the diameter of said intermediate shaft.

4. A surgical power tool as defined in claim 3 in which a seal retainer ring is disposed on said intermediate shaft between said second seal and said bearing.

5. A surgical power tool as defined in claim 2 in which said first and second seals are of material creating a static electric field as said intermediate shaft rotates.

6. A surgical power tool as defined in claim 1 in which said seal structure comprises first and second seals, said first seal being seated on and rotatable with said intermediate shaft and of an overall diameter slightly less than the internal bore of said sleeve, and said second seal being seated against the internal surface of said sleeve and having a hole through which said intermediate shaft passes slightly larger than the diameter of said intermediate shaft.

7. A surgical power tool as defined in claim 6 in which said first seal is slidable on said intermediate shaft.

8. A surgical power tool as defined in claim 7 in which said first and second seals are of material creating a static electric field as said intermediate shaft rotates.

9. A surgical power tool as defined in claim 6 in which a seal retainer ring is disposed on said intermediate shaft between said second seal and said bearing.

10. A surgical power tool as defined in claim 9 in which a driver is disposed on said intermediate shaft and is secured thereto by a set screw, and a pin extends between said driver and said first seal.

* * * * *